United States Patent
Taylor (10) Patent No.: US 6,358,233 B1
(45) Date of Patent: *Mar. 19, 2002

(54) ARCUATE ABSORBENT ARTICLE WITH LATERALLY EXTENDING FLAPS HAVING LONGITUDINAL STRETCH

(75) Inventor: Jo Ann Lee Taylor, Trenton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/614,759

(22) Filed: Mar. 13, 1996

(51) Int. Cl.⁷ ................................................. A61F 13/15
(52) U.S. Cl. ........................... 604/385.04; 604/385.01; 604/385.24; 604/387
(58) Field of Search .................. 604/358, 367, 604/373, 385.1–391, 385.04, 385.25–385.26

(56) References Cited

U.S. PATENT DOCUMENTS

| | | | |
|---|---|---|---|
| 3,860,003 A | | 1/1975 | Buell |
| 4,579,556 A | | 4/1986 | McFarland |
| 4,597,761 A | | 7/1986 | Buell |
| 4,608,047 A | * | 8/1986 | Mattingly ................. 604/387 |
| 4,668,230 A | | 5/1987 | Damico |
| 4,701,177 A | | 10/1987 | Ellis et al. |
| 4,911,701 A | * | 3/1990 | Mavinkurve ............... 604/387 |
| 4,940,462 A | * | 7/1990 | Salerno .................... 604/387 |
| 5,032,121 A | | 7/1991 | Mokry |
| 5,037,417 A | * | 8/1991 | Ternstrom et al. .......... 604/387 |
| 5,125,918 A | * | 6/1992 | Seidy ..................... 604/385.1 |
| B14,589,876 | | 4/1993 | Van Tilburg |
| 5,234,422 A | | 8/1993 | Sneller et al. |
| 5,518,801 A | * | 5/1996 | Chappell et al. ........... 604/387 |
| 5,591,147 A | * | 1/1997 | Couture-Dorschner et al. .. 604/385.1 |

FOREIGN PATENT DOCUMENTS

| | | | |
|---|---|---|---|
| EP | 0 091 412 | 10/1983 | |
| EP | 0 534 488 | 3/1993 | |
| EP | 0 590 675 | 4/1994 | |
| GB | 2 168 253 | 6/1986 | |
| GB | 2 289 417 | 11/1995 | |
| GB | 2 296 445 | 7/1996 | |
| JP | 5269169 | * 10/1993 | ............... 604/385.2 |
| JP | 5345001 | * 12/1993 | ............... 604/385.2 |
| WO | 95/08311 | 3/1995 | |
| WO | 95/08972 | 4/1995 | |
| WO | 95/20931 | 8/1995 | |
| WO | 96/10977 | 4/1996 | |

OTHER PUBLICATIONS

Translation of Zuikov '001.*
Translation of Zuikov '169.*

* cited by examiner

Primary Examiner—John G. Weiss
Assistant Examiner—K. M. Reichle
(74) Attorney, Agent, or Firm—Theodore P. Cummings; Matthew P. Fitzpatrick; Kevin C. Johnson (57) ABSTRACT

Absorbent articles, particularly sanitary napkins, having elastically extensible, laterally extending flaps are disclosed. The flaps are further provided with an adhesive for attaching them to a wearer's panty. At least a portion of the elastic extensibility has a vector component in the longitudinal direction. This longitudinally oriented elastic extensibility provides a contractive force which causes the absorbent article to assume an arcuate shape that more readily conforms to the wearer. Further, the extensibility allows the flaps to extend and contract with the edges of the leg openings of the wearer's panty so the flaps are more reliably adhered to the panty.

19 Claims, 2 Drawing Sheets

ARCUATE ABSORBENT ARTICLE WITH LATERALLY EXTENDING FLAPS HAVING LONGITUDINAL STRETCH

FIELD OF THE INVENTION

The invention disclosed herein relates to disposable absorbent articles, particularly sanitary napkins, and more particularly to sanitary napkins with laterally extending flaps having longitudinal stretch which provides curvature to the sanitary napkin for improved bodily fit while, at the same time providing protection against soiling and improved adherence to a wearer's panty.

BACKGROUND OF THE INVENTION

Catamenial pads, such as sanitary napkins, and related disposable absorbent articles which provide for the collection of menses and other bodily discharges are well known in the art. It has long been an object of the art to provide sanitary napkins which readily intercept menses upon discharge from the wearer.

Unitary disposable absorbent articles such as catamenial pads or incontinent pads all have the same basic structure. An absorbent core is encased between a liquid pervious topsheet and a liquid impervious backsheet. Numerous variations of and elements in addition to the basic topsheet, backsheet, and absorbent core arrangements are known. Each additional element is usually directed to improving a specific characteristic of the catamenial pad or incontinent pad.

Disposable absorbent articles have been provided with elastic members to improve the side leakage performance of such products. U.S. Pat. No. 3,860,003, issued to Buell on Jan. 14, 1975, discloses elasticized disposable absorbent articles wherein an elastic member is positioned in the side flap of the product between the topsheet and the backsheet. The elasticized portion of each side flap is positioned sufficiently remote from the semi-rigid absorbent body to permit an elasticized contractible line through the side flap. The side flap is gathered by the elastic member such that a boat-like configuration for the pad is presented and the side flaps form a barrier along the edges of the product. In particular, FIG. 5 and FIG. 6 of the Buell patent show incontinent pads having various shaped absorbent cores wherein an elastic member is positioned along the side edges of the product.

European Patent Application 0 091 412 A2, published on Oct. 12, 1983, in the name of Widlund, adopts the configuration shown in the Buell '003 patent and specifically relates it to a feminine hygiene product. The Widlund application teaches a sanitary napkin with elastic means spaced from the core to thereby raise and form barriers against lateral leakage from the product. FIG. 1 of the Widlund patent shows the boat-like shape of the product with the side flaps forming lateral barriers to the flow of exudates.

U.S. Pat. No. 4,597,761 issued to Buell on Jul. 1, 1986, discloses an elasticized insert product for use as an incontinent pad or sanitary napkin having elastic in the side flaps. One or more elastic strands are positioned in the side flap to allow the product to assume the boat-like configuration shown in FIG. 1 with the side flaps extending upwardly to form barrier walls against lateral leakage.

U.S. Pat. No. 4,579,556 issued to McFarland on Apr. 1, 1986, further defines the Buell '003 concept for incontinent pads by creating a dual baffle structure at the edges. The impervious backing sheet is folded over the topsheet and the absorbent layer and fastened to the topsheet so that when the elastic contracts, the pad bows with the elasticized fold raising above the surface of the pad to form a baffle. A lower baffle is formed over the absorbent with the upstanding baffle containing the elastic.

U.S. Pat. No. 4,668,230 issued to D'Amico et al. on May 26, 1987, adopts the Buell '003 approach and the Widlund application approach by extending the elastics to the ends of the pad and allowing the pad to assume a cup-like or boat-like shape. In particular, the elastics are secured at one end of the pad and extend at least two-thirds of the length of the remainder of the pad to give the proper trough-like shape to the pad. However, side flaps that stand up are not created in the D'Amico et al. patent.

UK Patent Application 2 168 253A, Baird and Robert published on Jun. 18, 1986, discloses an incontinent pad or sanitary napkin provided with liquid impermeable upwardly folded side flaps. The side flaps are formed by extending the backsheet beyond the absorbent core along at least part of the lateral edges of the absorbent core. A seal is formed adjacent the side edge of the absorbent core to present a dual baffle against leakage in the sides of the pad.

U.S. Pat. No. 4,701,177 issued to Ellis et al. on Oct. 20, 1987, provides a pad that is generally thicker in the center portion than at the ends of the pad. The upstanding side portions in the middle of each longitudinal edge are in the area where the absorbent core is hourglass or narrower shaped. The pad is also curved into a boat-like shape to generally conform to the pudendum of the wearer. The elastic film members are secured in the side flap of the sanitary napkin or incontinent pad between the topsheet and the backsheet to form the upstanding baffles.

U.S. Pat. No. 5,032,121 issued to Mokry on Jul. 16, 1991 adopts the Buell '003 and Widlund approach by placing the elasticized baffles in an hourglass-shaped pad with an hourglass-shaped absorbent core. The sanitary napkin includes a pair of elastic members affixed between the cover and the backsheet outward of the seal line and aligned adjacent to the central portion of the core. The elastic members cause the pad to acquire a cup-shaped configuration which corresponds to the perineal area of the user.

U.S. Pat. No. 5,234,422 issued to Sneller, et al. on Aug. 10, 1993 improves on earlier articles by wrapping the edges of the topsheet and the backsheet with an elasticized member. This elasticized member is preferably a laminate of an elastomeric layer and a coverstock layer. Since the coverstock layer is on the outside of the product, the sanitary napkin is provided with soft longitudinal edges which contact the wearer during use.

Each of these patents is related to providing elasticization in a sanitary napkin or incontinent pad. In each of these concepts, the elastic members are positioned in the side flap between the topsheet and the backsheet to allow the side flap to be gathered and to form upstanding baffles along the side edges of the product to slow or stop the lateral flow of body exudates beyond the edge of the pad. However, since the baffles slow or stop the lateral leakage by forming a seal between the baffle and the wearer's body, there is still a risk of leakage and resultant soiling of a wearer's undergarments due to seal failure.

Another approach to providing sanitary napkins with improved means for protection of a wearer's undergarment is found in U.S. Pat. No. B1 4,589,876 Reexamination Certificate issued Apr. 27, 1993 to Van Tilburg. This patent describes a sanitary napkin with flaps that extend laterally from a longitudinal edge of a central absorbent core. The flaps wrap around the crotch portion of the undergarment preventing soiling thereof.

One of the embodiments of U.S. Pat. No. 4,911,701 issued to Mavinkurve on Mar. 27, 1990 describes a catamenial with longitudinally disposed elastic strips in a pair of laterally extending flaps. The elastic strips cause the flaps to assume a concave configuration on their garment facing side. This concave configuration is said to provide greater resistance to buckling when the panty is raised by a wearer. The invention is also said to provide a convex shape to the body facing portion of the sanitary napkin and allow adhesive free placement of the flaps.

U.S. Pat. No. 4,940,462 issued to Solerno on Jul. 10, 1990 discloses a sanitary napkin having expandable flaps. The expandable flaps are made of a stretchable material. This stretchability is said to allow the flaps to extend along the full length of the sanitary napkin without bunching. While the Solerno patent mentions the use of attachment adhesives, the type and location of such adhesives is unclear.

While the laterally extending flaps described in the above patents provide protection against soiling by covering the sides of a wearer's panties, they are not designed to conform to a wearer's anatomy in the pudendal region. Further, although the articles described in the Mavinkurve and Solerno patents are said to have longitudinally directed extensibility, this extensibility fails to provide a shape to the article offering such improved conformity.

It is particularly desirable to improve the wearing comfort of catamenial pads while preventing increased soiling of the garments surrounding the pad. Therefore, it is an object of the present invention to provide a disposable absorbent article providing improved protection against soiling while providing improved wearer comfort. It is a further object of the present invention to provide an elasticized catamenial pad or incontinence pad that protects against lateral soiling while improving the wearer's comfort by better conforming to the shape of the pudendal region. Also, it is an object of this invention to provide a sanitary napkin having an arcuate shape that more readily conforms to a wearer's body. Finally, it is an object of this invention to provide a sanitary napkin having elasticized flaps with longitudinal extensibility which not only provide an arcuate shape to the sanitary napkin but also provide improved adherence to a wearer's panty.

SUMMARY OF THE INVENTION

According to the present invention a unitary disposable absorbent article, such as a catamenial pad or an incontinent pad, is provided with laterally extending flaps having longitudinally oriented elastic extensibility. The flaps are joined to and extend laterally outboard of the longitudinal edges of a central absorbent body. In a preferred sanitary napkin embodiment of the present invention the central absorbent body comprises a fluid permeable topsheet, a fluid impermeable backsheet, an absorbent core disposed between the topsheet and the backsheet, and an acquisition component disposed between the absorbent core and the topsheet and the laterally extending, elastically extensible flaps comprise a separate, mechanically prestrained laminate of a flap cushion material, a flap barrier material and a flap elastic. The central absorbent body and the flaps of the preferred embodiment of the present invention are also provided with means for attaching the sanitary napkin to a wearer's panty. The flaps are joined to the central absorbent body in a longitudinally stretched condition such that, when the flaps return to their unstretched condition, the sanitary napkin is provided with an arcuate shape which more readily conforms to the shape of a wearer's pudendal region. The longitudinally oriented elastic extensibility of the flaps also results in improved reliability of the panty attachment means because the flaps can extend and contract along with the panty in response to normal wearer movements.

BRIEF DESCRIPTION OF THE DRAWINGS

While the specification concludes with claims particularly pointing out and distinctly claiming the present invention, it is believed the same will be better understood from the following description taken in conjunction with the accompanying drawings wherein like parts are given the same reference numeral, and:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and pad.

Figure 1:
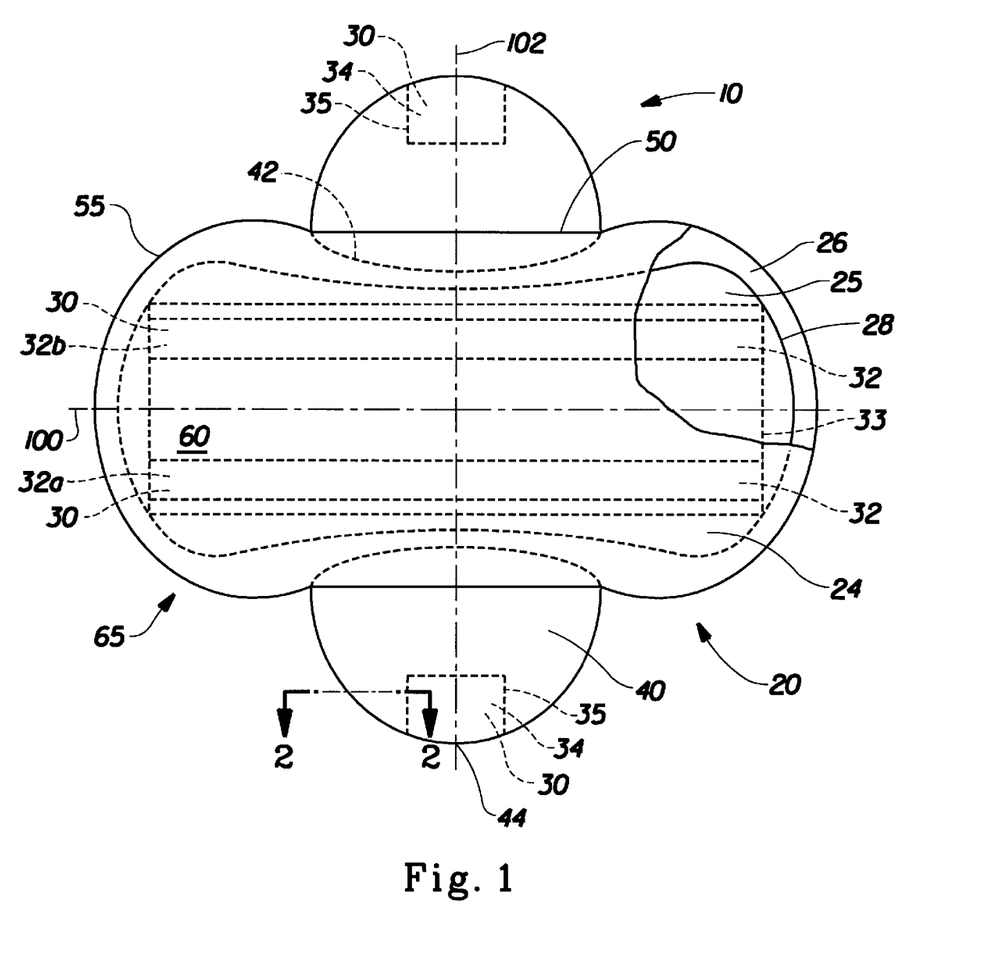
FIG. 1 is a top plan view, partially shown in cutaway, of a sanitary napkin according to the present invention.

A preferred embodiment of a unitary disposable absorbent article of the present invention is the catamenial pad, sanitary napkin 10, shown in FIG. 1. As used herein, the term "sanitary napkin" refers to an absorbent article which is worn by females adjacent to the pudendal region, generally external to the urogenital region, and which is intended to absorb and contain menstrual fluids and other vaginal discharges from the wearer's body (e.g., blood, menses, and urine). Interlabial devices which reside partially within and partially external of the wearer's vestibule are also within the scope of this invention. As used herein, the term "pudendal" refers to the externally visible female genitalia. It should be understood, however, that the present invention is also applicable to other feminine hygiene or catamenial pads such as pantiliners, or other absorbent articles such as incontinence pads, and the like.

FIG. 1 is a plan view of the sanitary napkin 10 of the present invention in its flat-out state with portions of the structure being cut-away to more clearly show the construction of the sanitary napkin 10 and with the portion of the sanitary napkin 10 which faces or contacts the wearer, oriented towards the viewer. The sanitary napkin 10 has two sides, a body-contacting side 60 or "body side" and a garment side 65. The sanitary napkin 10 is shown in FIG. 1 as viewed from its body side. The body side is intended to be worn adjacent to the body of the wearer while the garment side is on the opposite side and is intended to be placed adjacent to the wearer's undergarments when the sanitary napkin 10 is worn. As shown in FIG. 1, the sanitary napkin 10 preferably comprises a central absorbent body 20 and a pair of laterally extending, elastically extensible flaps 40.

The central absorbent body 20 comprises a liquid pervious topsheet 24, a liquid impervious backsheet 26 joined with the topsheet 24, and an absorbent core 28 positioned between the topsheet 24 and the backsheet 26. FIG. 1 also shows that the central absorbent body 20 has a periphery which is defined by the outer edges of the central absorbent body 20 in which the longitudinal edges are designated 50 and the end edges are designated 55. The central absorbent body 20 further has a longitudinal centerline 100 and a transverse centerline 102. The term "longitudinal", as used herein, refers to a line, axis or direction in the plane of the sanitary napkin 10 that is generally aligned with (e.g., approximately parallel to) a vertical plane which bisects a standing wearer into left and right body halves when the sanitary napkin 10 is worn. The terms "transverse" or "lateral" as used herein, are interchangeable, and refer to a line, axis or direction which lies within the plane of the sanitary napkin 10 that is generally perpendicular to the longitudinal direction.

While the topsheet, the backsheet, and the absorbent core may be assembled in a variety of well known configurations (including so called "tube" products), preferred sanitary napkin configurations are described generally in U.S. Pat. No. 4,950,264, issued to Osborn on Aug. 21, 1990; U.S. Pat. No. 4,425,130, issued to Desmarais on Jan. 10, 1984; U.S. Pat. No. 4,321,924, issued to Ahr on Mar. 30, 1982; U.S. Pat. No. 4,589,876, issued to Van Tilburg on Aug. 18, 1987, U.S. Pat. No. 5,009,653 issued to Osborn on Apr. 23, 1991, and U.S. Pat. No. 5,308,346 issued to Sneller, et al. on May 3, 1994. The disclosure of each of these patents is hereby incorporated herein by reference. FIG. 1 shows a preferred embodiment of the sanitary napkin 10 in which the topsheet 24 and the backsheet 26 have length and width dimensions generally larger than those of the absorbent core 28. The topsheet 24 and the backsheet 26 extend beyond the edges of the absorbent core 28 to thereby form portions of the periphery.

The topsheet 24 is compliant, soft feeling, and non-irritating to the wearer's skin. Further, the topsheet 24 is liquid pervious permitting liquids (e.g., menses and/or urine) to readily penetrate through its thickness. A suitable topsheet 24 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. A preferred topsheet comprises an apertured formed film. Apertured formed films are preferred for the topsheet because they are pervious to body exudates and yet are non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel. et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr et al. on Jul. 31, 1984; and U.S. Pat. No. 5,006,394 "Multilayer Polymeric Film" issued to Baird on Apr. 9, 1991. Each of these patents is incorporated herein by reference. The preferred topsheet for the present invention is the formed film described in one or more of the above patents and marketed on sanitary napkins by The Procter & Gamble Company of Cincinnati, Ohio as "DRI-WEAVE".

In a preferred embodiment of the present invention, the body side of the formed film topsheet is hydrophilic so as to help liquid to transfer through the topsheet faster than if the body side was not hydrophilic so as to diminish the likelihood that menstrual fluid will flow off the topsheet rather than flowing into and being absorbed by the absorbent core. In a preferred embodiment, the topsheet can be made hydrophilic by treating it with a surfactant such as is described in the above referenced U.S. Pat. Nos. 4,950,264 and 5,009,653 both issued to Osborn.

The absorbent core 28 may be any absorbent means which is capable of absorbing or retaining liquids (e.g., menses and/or urine). As shown in FIG. 1, the absorbent core 28 has a body surface, a garment surface, side edges, and end edges. The absorbent core 28 may be manufactured in a wide variety of sizes and shapes (e.g., rectangular, oval, hourglass, dog bone, asymmetric, etc.) and from a wide variety of liquid-absorbent materials commonly used in sanitary napkins and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these. The configuration and construction of the absorbent core may also be varied (e.g., the absorbent core may have varying caliper zones or be profiled so as to be thicker in the center), hydrophilic gradients, superabsorbent gradients, or lower density and lower average basis weight acquisition zones; or may comprise one or more layers or structures). The total absorbent capacity of the absorbent core should, however, be compatible with the design loading and the intended use of the sanitary napkin. Further, the size and absorbent capacity of the absorbent core may be varied to accommodate different uses such as incontinence pads, pantiliners, regular sanitary napkins, or overnight sanitary napkins.

Exemplary absorbent structures for use as the absorbent core of the present invention are described in U.S. Pat. No. 4,610,678 entitled "High-Density Absorbent Structures" issued to Weisman et al. on Sep. 9, 1986; U.S. Pat. No. 4,834,735 entitled "High Density Absorbent Members Having Lower Density and Lower Basis Weight Acquisition Zones", issued to Alemany et al. on May 30, 1989; and European Patent Application No. 0 198 683, The Procter & Gamble Company, published Oct. 22, 1986 in the name of Duenk, et al. A preferred embodiment of the absorbent core 28 of the present invention comprises a layer of superabsorbent material disposed between two air laid tissues as described in U.S. Pat. No. 4,950,264 entitled "Thin, Flexible Sanitary Napkin" issued to Osborn on Aug. 21, 1990 and U.S. Pat. No. 5,009,653 entitled "Thin, Flexible Sanitary Napkin" issued to Osborn on Apr. 23, 1991. The disclosure of each of these patents is incorporated herein by reference.

Figure 2:
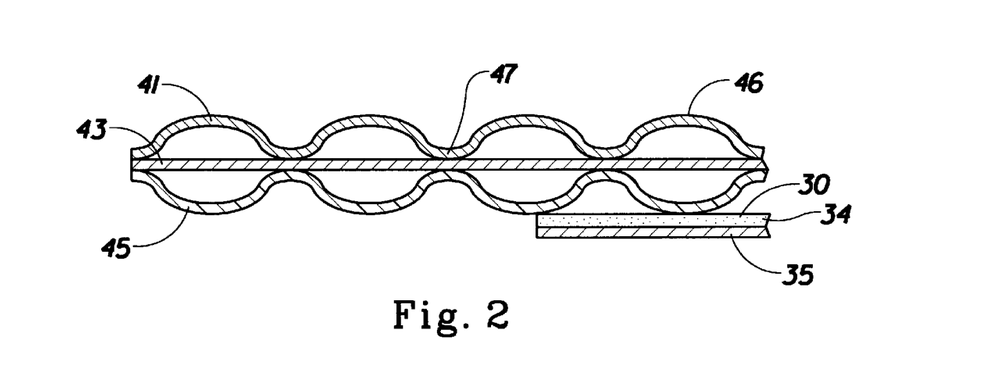
FIG. 2 is an expanded sectional view taken along lines 2—2 of FIG. 1, showing a preferred embodiment of the elastically extensible flap of the present invention.

In the preferred embodiment of the present invention shown in FIGS. 1 and 2, an acquisition component (or components) 25 may either be positioned between the topsheet 24 and the absorbent core 28, or comprise the bottom surface of a composite topsheet. The acquisition component may serve several functions. These functions include improving wicking of exudates over and into the absorbent core. The improved wicking of exudates is important because it provides a more even distribution of the exudates throughout the absorbent core and allows the sanitary napkin 10 to be made relatively thin. (The wicking referred to herein may encompass the transportation of liquids in one, two, or all directions (i.e., in the x-y plane and/or in the z-direction). The acquisition component may be comprised of several different materials including non-woven or woven webs of synthetic fibers including polyester, polypropylene, or polyethylene; natural fibers including cotton or cellulose; blends of such fibers; or any equivalent materials or combinations of materials. Examples of sanitary napkins having an acquisition component are more fully described in the above-referenced U.S. Pat. Nos. 4,950,264 and 5,009,653, and PCT Patent Publication WO 93/11725 "Absorbent Article Having Fused Layers", issued to Cree, et al. and now abandoned U.S. patent application Ser. No. 08/239,084 filed May 6, 1994. Each of these references is incorporated herein by reference. In a preferred embodiment, the acquisition component may be joined with the topsheet by any of the conventional means for joining webs together, most preferably by fusion bonds as is more fully described in the above-referenced Cree et al. patent application.

The backsheet 26 is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the sanitary napkin 10 such as pants, pajamas and undergarments. The backsheet 26 may thus comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Tredegar Film Products of Terre Haute, Ind., under the designation XP-39385. The backsheet is preferably embossed and/or matte finished to provide a more clothlike appearance. Further, the backsheet 26 may permit vapors to escape from the absorbent core 28 (i.e., breathable) while still preventing exudates from passing through the backsheet 26.

The backsheet 26 and the topsheet 24 are positioned adjacent the garment side and the body side, respectively, of the absorbent core 28 and are preferably joined thereto and to each other by attachment means (not shown) such as those well known in the art. For example, the backsheet 26 and/or the topsheet 24 may be secured to the absorbent core 28 or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031. The attachment means will preferably comprise an open pattern network of filaments of adhesive as is disclosed in U.S. Pat. No. 4,573,986 entitled "Disposable Waste-Containment Garment", which issued to Minetola, et al. on Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. The disclosure of each of these patents is incorporated herein by reference. Alternatively, the attachment means may comprise heat bonds, pressure bonds, ultrasonic bonds, dynamic mechanical bonds, or any other suitable attachment means or combinations of these attachment means as are known in the art.

In use, the sanitary napkin 10 can be held in place by any attachment means 30 well-known for such purposes. The attachment means 30 may be a mechanical fastener or, preferably, a pressure sensitive adhesive is used to secure the sanitary napkin 10 to a wearer's undergarment. The adhesive provides a means for securing the sanitary napkin in the crotch portion of the undergarment. Thus, a portion or all of the garment side 65 of the sanitary napkin 10 may be coated with adhesive. For the preferred embodiment of the present invention shown in FIGS. 1 and 2, this adhesive is disposed on both the central absorbent body 20 and the laterally extending flaps 40 of the sanitary napkin 10. That portion of the adhesive disposed on the central absorbent body 20 is identified as the pad adhesive 32 and that portion disposed on the flaps 40 is identified as the flap adhesive 34.

In the preferred embodiment of the sanitary napkin 10 shown in FIG. 1 the pad adhesive 32 comprises two longitudinally extending strips 32a and 32b which are disposed on the garment facing side 65 of the central absorbent body 20. As is shown in FIG. 1, each adhesive strip 32a and 32b lies adjacent one longitudinal edge of the absorbent core 28 and extends longitudinally along the full longitudinal length of the core. Any adhesive or glue used in the art for such purposes can be used for the adhesive herein, with pressure-sensitive adhesives being preferred. Suitable adhesives are Century A-305-IV manufactured by the Century Adhesives Corporation of Columbus, Ohio; and Instant Lock 34-2823 manufactured by the National Starch and Chemical Company of Bridgewater, N.J. Suitable adhesive fasteners are also described in U.S. Pat. No. 4,917,697.

The laterally extending flaps 40 also have means 30 for attaching one surface of the flap 40 to the wearer's undergarment or to the other flap 40. Preferably, as shown most clearly in FIG. 2, such attachment means 30 comprise the flap adhesive 34. The flap adhesive 34 is disposed on the face of the flap 40 which is oriented away from the topsheet 24 when the flaps 40 are in the flat out configuration of FIG. 1 (i. e.g., the garment facing side 65). As a result, when the flaps 40 are wrapped around the crotch portion of the wearer's undergarment, the flap adhesive 34 will face the outside of the wearer's undergarment. While adhesives similar to those used for the pad adhesive 32 may also be used as the flap adhesive 34, the flap adhesive 34 preferably comprises an elastically extensible adhesive film such as, such as Findley adhesive 198-338 supplied by Findley Adhesives of Wauwatosa, Wis. Alternatively, a non elastically extensible adhesive can be applied in a plurality of narrow transversely-oriented stripes so as not to interfere with the elastic extensibility of the flap 40 (discussed in detail below).

The pressure-sensitive adhesive is typically covered with a removable release liner in order to keep the adhesive from adhering to a surface other than the crotch portion of the undergarment prior to use. These are identified as the pad release liner 33 and the flap release liner 35 in FIGS. 1 and 2. Any commercially available release liners commonly used for such purposes can be utilized herein. Non-limiting examples of suitable release liners are BL30MG-A Silox E1/0 and BL30MG-A Silox 4P/O both of which are manufactured by the Akrosil Corporation of Menasha, Wis. Suitable release liners are also described in the above-referenced U.S. Pat. No. 4,917,697.

The sanitary napkin 10 further comprises at least one elastically extensible flap 40 which extends laterally outward from a longitudinal edge 50 of the central absorbent body 20. Preferably, one flap 40 extends from each longitudinal edge 50 of the central absorbent body 20 as is shown in FIG. 1. Each flap 40 extends away from the longitudinal axis 100 of the central absorbent body 20 of the sanitary napkin 10 in a direction parallel to the transverse axis 102 and is elastically extensible with at least a vector component in the longitudinal direction. As is shown most clearly in FIG. 3, the elastically extensible flaps 40 provide a contractive force which causes the sanitary napkin 10 to assume an arcuate shape. This arcuate shape allows the sanitary napkin 10 to more closely conform to the curvature of a wearer's body in the pudendal region. As a result, fit and comfort are improved and leakage is reduced.

Figure 3:
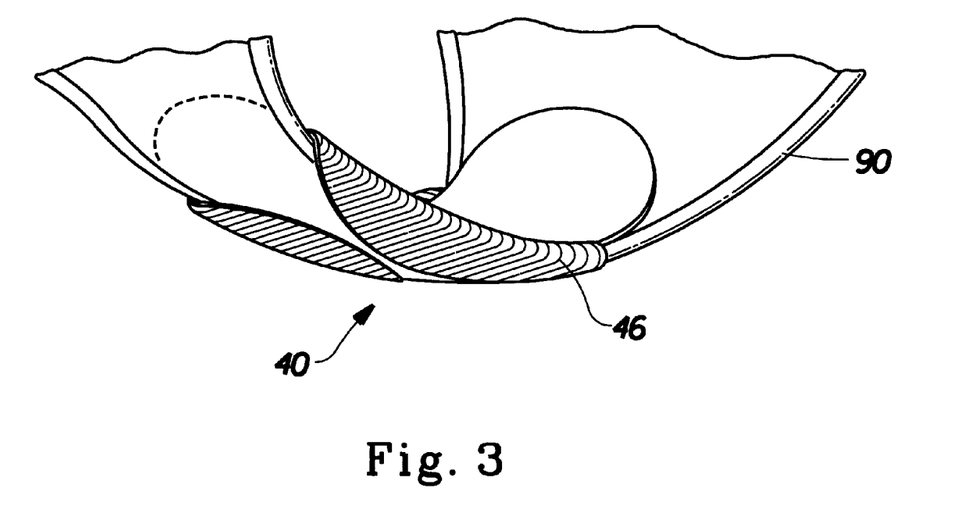
FIG. 3 is a perspective view of a sanitary napkin according to the present invention showing the arcuate shape thereof and demonstrating how the laterally extending flaps wrap the edges of a wearer's panties in the crotch region.

Further, also as shown in FIG. 3, the flaps 40 wrap around the edges 90 of the leg openings of a wearer's panties in the crotch region of the panties providing additional protection against soiling. Since the flaps 40 are elastically extensible, they are also able to extend and contract in response to normal wearer movement. As a result, the flaps 40 more reliably adhere to the wearer's panties throughout the normal range of wearer movement. Such adherence is enhanced by providing a flap adhesive 34 that can also expand and contract in response to wearer movement.

The flaps 40 have a proximal edge 42 which may be coincident with the juncture of attachment to the longitudinal edge 50 of the central absorbent body 20 or, the proximal edge 42 may be joined to the central absorbent body 20 at another location. Preferably, the proximal edge 42 is disposed between the topsheet 24 and the backsheet 26 slightly inboard of the longitudinal edge 50. This provides a small portion of each flap 40 that is also disposed between the topsheet 24 and the backsheet 26 for joining the flap 40 to the central absorbent body 20. The flaps 40 extend laterally outwardly from the central absorbent body 20 and terminate at a distal edge 44 which represents the point furthest from the longitudinal centerline 100 of the sanitary napkin 10. The flaps 40 may be of any shape desired, with a particularly preferred shape being shown in FIG. 1.

The flaps 40 each can comprise an integral and contiguous extension of the topsheet 24, the backsheet 26, or a laminate of both. Preferably, the flaps 40 each may comprise a separate and independent components that may then be joined to the central absorbent body adjacent a longitudinal edge 50 thereof. This separate and independent component may comprise the same materials as are used to form either the topsheet or the backsheet or both or it may comprise different individual materials or laminates of different materials. More preferably, each flap 40 comprises a laminate of three laminae and is a separate and independent component that is joined to the central absorbent body 20 adjacent a longitudinal edge 50 thereof. The preferred laminate is shown most clearly in FIG. 2.

The lamina on the body-contacting side 60 of the sanitary napkin 10, the flap cushion 41, is compliant, soft feeling and non-irritating to a wearer's skin. Suitable materials are essentially the same as those suitable for the topsheet 24. Preferably, the flap cushion 41 comprises the same apertured, formed thermoplastic film as is used for the topsheet 24.

The lamina on the garment side, the flap barrier 45, is impervious to liquids to prevent body liquids that may wick beyond the lateral edges 50 of the central absorbent body 20 from staining the wearer's panty. Suitable materials include thin plastic films; impervious woven or nonwoven materials; and composite materials. Preferably, the flap barrier 45 comprises the same 0.012 mm (0.5 mil) to about 0.051 mm (2.0 mils) polyethylene film as is used for the backsheet 26. Alternatively, if the flap elastic 43 (discussed below) comprises an impervious material, the flap barrier 45 can also comprise a material substantially the same as is used for the flap cushion 41.

The third lamina of the preferred embodiment of a flap 40 of the present invention shown in FIG. 2, the flap elastic 43, lies between the flap cushion 41 and the flap barrier 45. The flap elastic 43 may comprise a number of different elastic materials. For example, the flap elastic 43 may comprise elastomeric films (including heat shrinkable elastomeric films as discussed below), "live" elastics of synthetic or natural rubber including films or strands of such elastic material, elastomeric foams (e.g., synthetic or natural rubber foams), elastomeric woven or nonwoven webs, formed elastic scrim, elastomeric adhesive, or other elastomeric materials as are known in the art. Preferably, the flap elastic 43 comprises an elastomeric film such as is marketed by Exxon of Paramus, N.J. under the designation EXX 500 1.5 mil elastic. Alternatively, the flap elastic 43 can comprise an elastically extensible adhesive film such as Findley adhesive 198-338 supplied by Findley Adhesives of Wauwatosa, Wis.).

Alternatively, the flap elastic 43 can be formed from materials which contract unidirectionally and become elastic following specific treatment such as heating. Elastic materials are known which can be heated to their transition temperature and stretched into an elongated orientation. They are then chilled and become relatively inelastic and fixed in their elongated orientation. Subsequent heating causes the materials to contract to their initial (uncontracted or relaxed) orientation and to regain their elasticity. Examples of such materials are shown in U.S. Pat. No. 3,819,401, issued Jun. 25, 1974 to Massengale, et al and U.S. Pat. No. 3,912,565, issued Oct. 14, 1975 to Koch, et al, the disclosures of both patents being incorporated herein by reference. When such materials are used as flap elastics 43, the flap cushion 41, the flap barrier 45, and the flap elastic are affixed together by attachment means as discussed below and joined to the central absorbent body 20 while all three are in uncontracted orientations. The system is then heated (as with heated air) and the elastic waist element is allowed to return to its relaxed or contracted orientation.

The flap cushion 41 and the flap barrier 45 are joined to the flap elastic 43 by attachment means (not shown) such as those well known in the art. For example, the flap cushion 41 and/or the flap barrier 45 may be secured to the flap elastic 43 or to each other by a uniform continuous layer of adhesive, a patterned layer of adhesive, or an array of separate lines, spirals, or spots of adhesive. The elastic attachment means are preferably a low modulus pressure sensitive adhesive, such as elastomeric, pressure sensitive adhesive Formula #198-338 as is manufactured by Findley Adhesives, Inc. of Wauwatosa, Wis. The flap elastic attachment means will preferably comprise an open pattern network of filaments of adhesive as is disclosed in U.S. Pat. No. 4,573,986 entitled "Disposable Waste-Containment Garment", which issued to Minetola, et al. on Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents is incorporated herein by reference. Alternatively, the attachment means may comprise heat bonds, pressure bonds, ultrasonic bonds, dynamic mechanical bonds, or any other suitable attachment means or combinations of these attachment means as are known in the art.

As noted above, at least one flap 40 is elastically extensible with at least a vector component in the longitudinal direction. As used herein the property "elastically extensible" is determined as follows. The component of the sanitary napkin 10 is tested and considered elastically extensible if the following test criterion is met.

To prepare a sample for testing, all release paper is removed from the sanitary napkin 10. Any exposed adhesive 32, 34 may be blocked with a suitable agent, such as corn starch. The flap 40, backsheet 26, or other component of the sanitary napkin 20 to be tested, is severed from the rest of the sanitary napkin 10, for example, by cutting along the proximal edge 42 of the flap 40 with scissors. The component to be tested is then cut to a preferred test specimen size of about 6.4 centimeters (gage length) by about 2.54 centimeters (width). If the component to be tested is too small to yield the preferred test specimen size, a smaller specimen may be tested.

The elastic extensibility may be measured with a Model 1122 tensile machine made by the Instron Engineering Corporation of Canton, Mass. Preferred jaws for this tensile machine are pneumatic action, coated, light duty, flat faced jaws Instron model number 3B. The sample to be tested is mounted in the tensile machine with the principal axis of elongation oriented in the tensile machine extension direction. The component of the sanitary napkin 10 to be tested is preferably inserted into each jaw of the tensile machine only a distance sufficient to prevent tearing out of the jaws upon the application of the tensile force.

The jaws are separated, without tensile loading the sample, until it is taut. All wrinkles, except designed pleats 46 and the like, should be removed. This defines the original jaw position of the sample.

The jaws are separated at a constant rate of about 100 centimeters per minute until an elongation of about 25 percent (1.25 times the original gage length) is reached. This procedure produces an extension stress-strain curve from the original gage length and jaw position to the extended position, and having the stress vector along the vertical axis and the strain vector along the horizontal axis. The area under this curve is calculated and hereinafter referred to as $A_1$. A suitable means for calculating the area under this curve is with a computer program such as is sold by Laboratory MicroSystems, Inc. of Troy, N.Y. under the name Mechanical Test Package.

The jaws are then returned to the original jaw position at a constant rate of about 100 centimeters per minute. This defines a relaxation stress-strain curve, from the extended position to the original gage length. The area under this stress-strain curve is also calculated and is hereinafter referred to as $A_2$.

The ratio of the area of the relaxation stress-strain curve to the area of the extension stress-strain curve, $A_2/A_1$, is then found and is hereinafter referred to as the relaxation-extension area ratio. The tested component of the sanitary napkin 10 is considered elastically extensible if the relaxation-extension area ratio is greater than or equal to about 0.6. More preferably, the tested component exhibits a relaxation-extension area ratio greater than or equal to about 0.75. The tested component is considered to be elastically extensible and within the intent and scope of the claimed invention if such component is mounted in the sanitary napkin 10 so that an axis of elastic extensibility has at least a 10° vector component in the longitudinal direction. If the relaxation extension area ratio is less than about 0.6, such as would likely and typically occur when the tested component of the sanitary napkin 10 rips, shreds, or undergoes unintended, excessive gross or plastic deformation, such a component of the sanitary napkin 10 is outside the intent and scope of the claimed invention.

In the preferred embodiment of the present invention shown in FIG. 2, at least a portion of the flap cushion 41 and the flap barrier 45 are subjected to mechanical stretching in order to provide a "zero strain" stretch laminate for the flaps 40 that is elastically extensible. The flap cushion 41 and the flap barrier 45 can be stretched by directing them through an incremental mechanical stretching system similar to the operation described with respect to the formation of the "zero strain" stretch laminates in U.S. Pat. No. 5,151,092 entitled "Absorbent Article With Dynamic Elastic Waist Feature Having A Predisposed Resilient Flexural Hinge", issued to Buell, et al., on Sep. 29, 1992. As is shown in FIG. 2, the flap 40 has been provided with discrete regions of securement 47 wherein the flap cushion 41 and the flap barrier 45 are joined by means familiar to the art to the elastic member 43. The flap 40 is shown in FIG. 2 in its relaxed state. In particular, the elastic member 43 is not stretched in this state. As a result, the mechanically stretched portions of the flap cushion 41 and the flap barrier 45 located between the regions of securement 47 form pleats 46.

Alternatively, the flaps 40 may comprise a structural elastic-like film (SELF) web. A structural elastic-like film web is an extensible material that exhibits an elastic-like behavior in the direction of elongation without the use of added elastic materials. The SELF web includes a strainable network having at least two contiguous, distinct, and dissimilar regions. One of the regions is configured so that it will exhibit resistive forces in response to an applied axial elongation in a direction parallel to the predetermined axis before a substantial portion of the other region develops significant resistive forces to the applied elongation. At least one of the regions has a surface-pathlength which is greater than that of the other region as measured substantially parallel to the predetermined axis while the material is in an untensioned condition. The region exhibiting the longer surface-pathlength includes one or more deformations which extend beyond the plane of the other region. The SELF web exhibits at least two significantly different stages of controlled resistive force to elongation along at least one predetermined axis when subjected to an applied elongation in a direction parallel to the predetermined axis. The SELF web exhibits first resistive forces to the applied elongation until the elongation of the web is sufficient to cause a substantial portion of the region having the longer surface-pathlength to enter the plane of applied elongation, whereupon the SELF web exhibits second resistive forces to further elongation. The total resistive forces to elongation are higher than the first resistive forces to elongation provided by the first region. SELF webs suitable for the present invention are more completely described in the copending, commonly assigned U.S. patent application Ser. No. 08/203, 456 entitled "Absorbent Article with Multiple Zone Structural Elastic-Like Film Web Extensible Waist Feature" filed by Donald C. Roe, et al. on Feb. 24, 1994, the disclosure of which is incorporated herein by reference.

The preferred mechanically prestrained flap 40 is then longitudinally stretched prior to joining it to the central absorbent body 20 such that the pleats 46 are at least partially pulled out so the flaps provide a contractive force which causes the central absorbent body to assume an arcuate configuration. The flap 40 may be stretched to any length suitable to cause the sanitary napkin 10 to assume an arcuate shape when worn without generating excessive forces that could cause wearer discomfort or adversely affect the shape of the sanitary napkin. It is preferred that the elongation may be relatively small so as not to cause bowing of the ends of the sanitary napkin. Generally, the flap 40 may be stretched from about 5% to about 100%, more preferably from about 10% to about 25%. In a preferred embodiment, the elastic member is stretched about 12.5% (112.5% of its original length) and then joined to the central absorbent body 20 adjacent the longitudinal edge 50 thereof.

The sanitary napkin 10 of the present invention is used by removing the pad release liner 33 and thereafter placing the sanitary napkin in an undergarment so that the pad adhesive 32a, 32b contacts the undergarment. The flap release liner 35 is then removed from both portions of flap adhesive 34 and the flaps 40 are attached to the wearer's panty or to each other. The adhesive maintains the sanitary napkin in its position within the undergarment during use.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A sanitary napkin for protecting an undergarment from soiling, said sanitary napkin comprising:
    a longitudinal centerline defining a longitudinal direction;
    a central absorbent body having a body-facing side, a transverse centerline and longitudinal edges, said central absorbent body further comprising:
        a liquid pervious topsheet;
        a liquid impervious backsheet joined with said topsheet;
        an absorbent core between said topsheet and said backsheet;
    means for attaching said central absorbent body to the undergarment disposed on said central absorbent body;
    a pair of laterally extending elastic flaps being elastically extensible in the longitudinal direction, wherein each of said elastic flaps comprises
        a first portion operating as a proximal edge being joined to said central absorbent body, said proximal edge being adjacent to a respective one of said longitudinal edges, and
        an extensible, elastic second portion extending laterally outwardly to a distal edge, said distal edge being positioned outwardly away from the central absorbent body of the sanitary napkin; and
        the second portion of the flap being elastically extensible with a vector component in the longitudinal direction, said elastic flaps being attached in a longitudinally extended condition to said central absorbent body at said first portion to provide a contractive force which causes said central absorbent body to assume an arcuate configuration about said transverse centerline wherein said body facing side of said central absorbent body has a concave configuration, said contractive force being caused by the extensible, elastic second portions of the elastic flaps; and
    means for attaching each of said flaps to the undergarment.

2. A sanitary napkin according to claim 1 wherein said laterally extending flaps are made of a discrete component.

3. A sanitary napkin according to claim 2 wherein said discrete component comprises a mechanically prestrained laminate.

4. A sanitary napkin according to claim 2 wherein said discrete component comprises a SELF web.

5. A sanitary napkin according to claim 1 wherein said longitudinally extended condition comprises longitudinal stretching between about 5 percent and about 100 percent.

6. A sanitary napkin according to claim 1 wherein said longitudinally extended condition comprises longitudinal stretching between about 10 percent and about 25 percent.

7. A sanitary napkin according to claim 1 wherein said longitudinally extended condition comprises longitudinal stretching of about 12.5 percent.

8. A sanitary napkin according to claim 1 wherein said laterally extending flaps comprise an integral and contiguous extension of said topsheet and said backsheet that are adhered together to form a laminate.

9. A sanitary napkin according to claim 1 wherein said means for attaching each of said flaps to the undergarment comprises an elastically extensible adhesive film.

10. A sanitary napkin according to claim 1 wherein said elastically extensible flaps have a relaxation-extension area ratio greater than about 0.75.

11. A sanitary napkin for protecting an undergarment from soiling, said sanitary napkin comprising:
    a longitudinal centerline defining a longitudinal direction;
    a central absorbent body having a body-facing side, a transverse centerline and longitudinal edges, said central absorbent body further comprising:
        a liquid pervious topsheet;
        a liquid impervious backsheet joined with said topsheet;
        an absorbent core between said topsheet and said backsheet;
    means for attaching said central absorbent body to the undergarment disposed on said central absorbent body;
    a pair of laterally extending flaps, said flaps being elastically extensible with at least a vector component in the longitudinal direction and having a contractive force which causes said central absorbent body to assume an arcuate configuration about said transverse centerline wherein said body facing side of said central absorbent body has a concave configuration, wherein each of said flaps has a proximal edge which is joined to said central absorbent body adjacent a respective one of said longitudinal edges in a longitudinally extended condition to create said contractive force and extends laterally outwardly therefrom to a distal edge, each of said flaps comprising a laminate of a flap cushion material, a flap barrier, and a flap elastic member; and means for attaching each of said flaps to the undergarment disposed on said flaps.

12. A sanitary napkin according to claim 11 wherein said laminate is mechanically prestrained.

13. A sanitary napkin according to claim 12 wherein said flap elastic member comprises an elastomeric film.

14. A sanitary napkin according to claim 12 wherein said flap elastic member comprises an elastically extensible adhesive film.

15. A sanitary napkin according to claim 11 wherein said laminate comprises a SELF laminate.

16. A sanitary napkin according to claim 1 wherein said longitudinally extended condition comprises longitudinal stretching between about 5 percent and about 100 percent.

17. A sanitary napkin according to claim 11 wherein said longitudinally extended condition comprises longitudinal stretching between about 10 percent and about 25 percent.

18. A sanitary napkin according to claim 11 wherein said longitudinally extended condition comprises longitudinal stretching of about 12.5 percent.

19. A sanitary napkin according to claim 11 wherein said means for attaching each of said flaps to the undergarment comprises an elastically extensible adhesive film.

* * * * *

UNITED STATES PATENT AND TRADEMARK OFFICE
CERTIFICATE OF CORRECTION

PATENT NO.     : 6,358,233 B1
DATED          : March 19, 2002
INVENTOR(S)    : Jo Ann Lee Taylor It is certified that error appears in the above-identified patent and that said Letters Patent is hereby corrected as shown below:

<u>Column 16,</u>
Line 3, change "1" to -- 11 --.

Signed and Sealed this

Twenty-seventh Day of August, 2002

Attest:

Attesting Officer

JAMES E. ROGAN
*Director of the United States Patent and Trademark Office*